(12) United States Patent  (10) Patent No.: US 7,833,279 B2
Knudson et al.  (45) Date of Patent: Nov. 16, 2010

(54) PANCREATIC EXOCRINE SECRETION DIVERSION APPARATUS AND METHOD

(75) Inventors: Mark B. Knudson, Shoreview, MN (US); Timothy R. Conrad, Eden Prairie, MN (US)

(73) Assignee: EnteroMedics Inc., St. Paul, MN (US)

( * ) Notice: Subject to any disclaimer, the term of this patent is extended or adjusted under 35 U.S.C. 154(b) by 292 days.

(21) Appl. No.: 10/987,369

(22) Filed: Nov. 12, 2004

(65) Prior Publication Data

US 2006/0106332 A1    May 18, 2006

(51) Int. Cl.
*A61F 2/04* (2006.01)
*A61M 5/00* (2006.01)

(52) U.S. Cl. ............... 623/23.64; 623/23.65; 623/23.68; 604/8; 604/9; 604/10

(58) Field of Classification Search ............... 623/23.64, 623/23.65, 23.68; 604/8–10; 606/171
See application file for complete search history.

(56) References Cited

U.S. PATENT DOCUMENTS

| | | | |
|---|---|---|---|
| 5,088,979 A | 2/1992 | Filipi et al. | |
| 5,199,430 A | 4/1993 | Fang et al. | |
| 5,231,988 A | 8/1993 | Wernicke et al. | |
| 5,263,480 A | 11/1993 | Wernicke et al. | |
| 5,514,175 A | 5/1996 | Kim et al. | |
| 5,540,730 A | 7/1996 | Terry et al. | |
| 6,097,984 A | 8/2000 | Douglas | |
| 6,302,917 B1 | 10/2001 | Dua et al. | |
| 6,341,236 B1 | 1/2002 | Osorio et al. | |
| 6,369,079 B1 | 4/2002 | Rubin et al. | |
| 6,449,511 B1 | 9/2002 | Mitchev et al. | |
| 6,558,708 B1 | 5/2003 | Lin | |
| 6,684,105 B2 | 1/2004 | Cohen et al. | |
| 6,853,862 B1 | 2/2005 | Marchal et al. | |
| 6,928,320 B2 | 8/2005 | King | |
| 6,993,391 B2 | 1/2006 | Flesler et al. | |
| 2003/0018367 A1 | 1/2003 | DiLorenzo | |

(Continued)

FOREIGN PATENT DOCUMENTS

WO    WO 01/41671 A2    6/2001

OTHER PUBLICATIONS

Printz, H. et al, "Intraoperative ultrasonography in surgery for chronic pancreatits", Int. J Gastroint Cancer, 12:3, 233-237, 1992.*

(Continued)

*Primary Examiner*—Melanie J Hand
(74) *Attorney, Agent, or Firm*—Merchant & Gould P.C.

(57) ABSTRACT

A method and apparatus for treating a patient's health condition by diverting pancreatic exocrine secretions include a flow diverter of material compatible with chronic residence within a small intestine of the patient. The flow diverter has a cover end and a discharge end. The flow diverter is sized to be placed within the small intestine with the discharge end placed distally from said cover end and with said flow diverter further sized so permit passage of chyme through the small intestine and past the flow diverter. The cover end is sized to cover a discharge papilla of the pancreatic duct. The diverter is adapted to divert at least a portion of pancreatic exocrine secretion from the papilla to the distal discharge end.

13 Claims, 3 Drawing Sheets

U.S. PATENT DOCUMENTS

| | | |
|---|---|---|
| 2003/0045909 A1 | 3/2003 | Gross et al. |
| 2004/0092892 A1* | 5/2004 | Kagan et al. ............... 604/264 |
| 2004/0107004 A1* | 6/2004 | Levine et al. ............ 623/23.64 |
| 2004/0167583 A1 | 8/2004 | Knudson et al. |
| 2004/0172085 A1 | 9/2004 | Knudson et al. |
| 2004/0172086 A1 | 9/2004 | Knudson et al. |
| 2004/0176812 A1 | 9/2004 | Knudson et al. |
| 2005/0038484 A1 | 2/2005 | Knudson et al. |
| 2005/0043817 A1* | 2/2005 | McKenna et al. ........ 623/23.65 |
| 2005/0070970 A1 | 3/2005 | Knudson et al. |
| 2005/0070974 A1 | 3/2005 | Knudson et al. |
| 2006/0036293 A1 | 2/2006 | Whitehurst et al. |
| 2006/0155375 A1* | 7/2006 | Kagan et al. ............ 623/11.11 |

OTHER PUBLICATIONS

Baron, et al., "Acute Necrotizing Pancreatitis", *New England J. of Medicine*, vol. 340, No. 18, pp. 1412-1417 (1999).

Chatzicostas, et al., "Balthazar computed tomography severity index is superior to Ranson criteria and APACHE II and II scoring systems in predicting acute pancreatitis outcome", *J. Clinical Gastroenterology*, 36(3), pp. 253-260 (2003).

Fazel et al., "Prophylactic Pancreatic Duct Stenting: A Panacea", *Gastroenterology*, vol. 124, No. 4, pp. 1274-1275 (2003).

Soran, et al., "Outcome and quality of life of patients with acute pancreatitis requiring intensive care", *J. Surg. Res.*, 91(1), pp. 89-94 (2000).

Steer et al., "Chronic Pancreatitis", *New England J. of Medicine*, pp. 1482-1490 (1995).

Kilgore, K. et al., "Nerve Conduction Block Utilising High-Frequency Alternating Current," *Medical & Biological Engineering & Computing*, vol. 42, pp. 394-406 (2004).

Product Brochure, "ATROSTIM Phrenic Nerve Stimulator," AtroTech Oy, P.O. Box 28, FIN-33721 Tampere, Finland, 2 pages (Jun. 2004).

\* cited by examiner

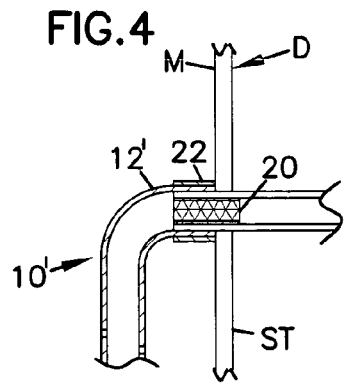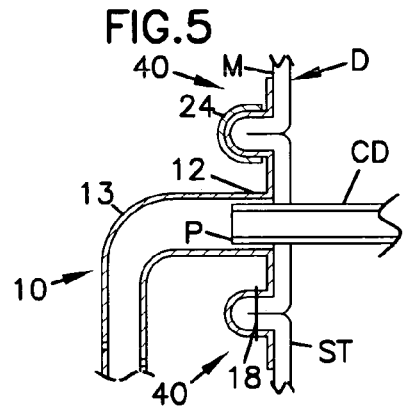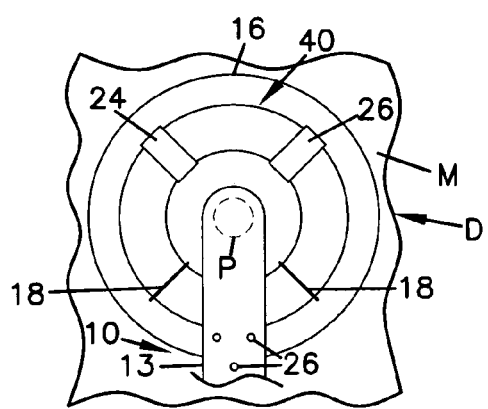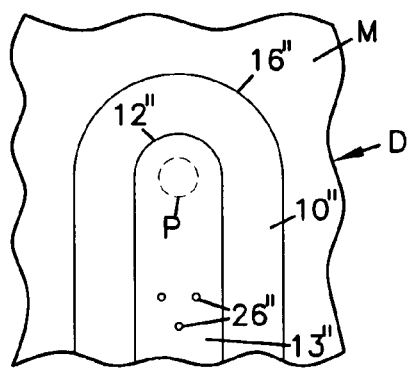

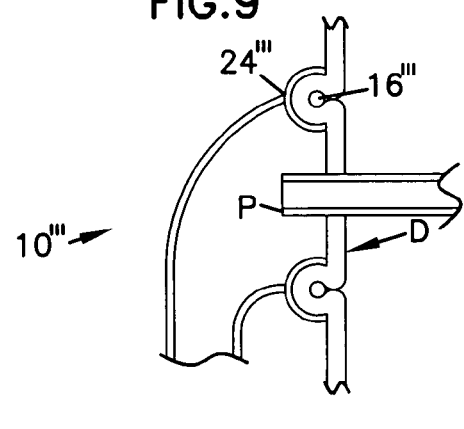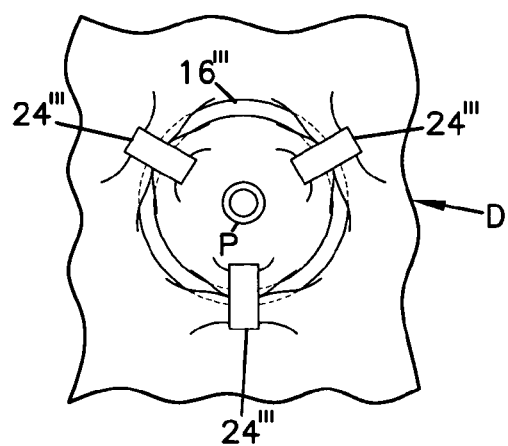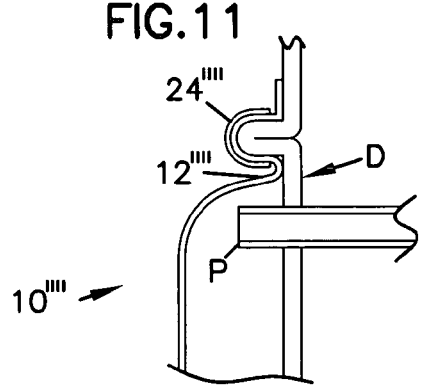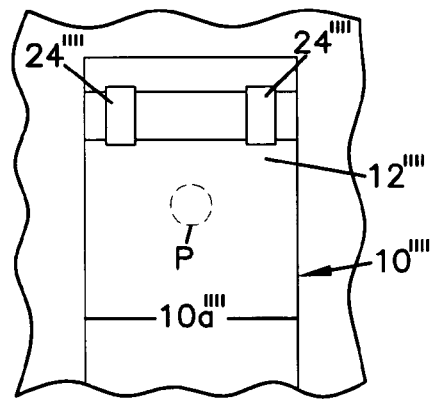

PANCREATIC EXOCRINE SECRETION DIVERSION APPARATUS AND METHOD

BACKGROUND OF THE INVENTION

1. Field of the Invention

This invention pertains to a method and apparatus for down-regulating nutrient absorption in a small intestine of a patient. More particularly, this invention pertains to an apparatus and method for promoting a down-regulation of nutrient absorption by diverting at least a portion of flow of pancreatic exocrine secretion to a distal location within the small intestine.

2. Description of Prior Art

Morbid obesity and its concurrent health risks (including diabetes, heart disease and other ailments) are of near-epidemic proportions in industrialized societies. A wide variety of treatments have been proposed and attempted to treat morbid obesity with a wide variety of efficacy and associated morbidity. These treatments include techniques to reduce stomach volume, alter gastric and intestinal motility, and alter the absorption of nutrients in the small intestine.

Gastric Volume Reduction

Surgical approaches to gastric volume reduction include minimally invasive surgery, open surgery and endoscopic approaches to gastric volume reduction. Many such procedures have been tried and some have been abandoned due to lack of efficacy or unacceptable morbidity and mortality.

The gastric volume reduction procedures include vertical and horizontal gastroplasty in which sutures, staples or other fixation devices are used to join opposing surfaces of the stomach to create a reduced volume pouch and thereby reduce caloric intake. Less invasive techniques are suggested for placing a band around an upper portion of the stomach to act as a belt to reduce the size of the stomach and create a small passageway (a stoma) from a small upper pouch to the remainder of the stomach. Other techniques for reducing gastric volume size include placement of obstructions within the stomach. These include intra-gastric balloons which are filled with saline to reduce the effective volume of the stomach.

Less invasive techniques for restricting the volume of the stomach also include a gastric partition in which the stomach wall is endoscopically cinched together to form a reduced size pouch. The cinching is performed using commercially available products such as the Bard EndoCinch™ and the Wilson-Cook Sew-Right™ cinching equipment. Such surgical equipment is generally described in U.S. Pat. No. 5,088,979 to Filipi et al. issued Feb. 18, 1992; U.S. Pat. No. 6,302,917 to Dua et al. issued Oct. 16, 2001 or PCT International Publication No. WO 01/89393 published Nov. 29, 2001.

It has been recognized that gastric volume reduction does not address all mechanisms associated with obesity. For example, patients with gastric volume reduction can defeat the effectiveness of the gastric volume reduction by modifying eating habits. For instance, a patient may graze continuously on small volume, high caloric food or may replace solid foods with high caloric liquid foods.

Malabsorption Treatments

To address deficiencies associated with gastric volume reduction, treatments have been suggested and developed for reducing the amount of nutrient absorption in the small intestine (particularly in the upper and middle portions of the small intestine—the duodenum and jejunum, respectively).

In the duodenum, ducts from the pancreas and gall bladder discharge into the small intestine through small protrusions referred to as papilla. Commonly, pancreatic exocrine secretions ("PES") flow from the pancreas in a pancreatic duct. Similarly, bile from the gall bladder flows through a bile duct. These ducts merge to form a common duct with discharges through a papilla into the duodenum. In some patients, the bile duct and pancreatic duct do not merge and separately discharge into the duodenum at separate papilla which, usually, are in close proximity to one another.

Techniques to reduce nutrient absorption (commonly referred to as malabsorption treatments) include drug therapies for reducing lipids absorption. Such drug therapies have uncomfortable side effects, which can discourage a patient from complying with the drug therapy. Other techniques include surgical techniques for rerouting the intestinal system to bypass an extended portion of the small intestine. These include a so-called jejunoileal bypass. Not commonly used due to unacceptable mortality rates, a jejunoileal bypass would result in effective weight loss. Other techniques include the gastric bypass (or Roux-en Y) and duodenal switch. In both of these procedures, a large segment of the small intestine (including the duodenum) are bypassed so that food content is rerouted from a small pouch formed in the upper portion of the stomach to the jejunum. As a result, the absorptive length of the small intestine is significantly shortened thereby reducing the amount of nutrients which are absorbed into the body and which support or lead to weight gain. These procedures combine the benefits of gastric volume reduction with malabsorption. Unfortunately, such surgical procedures are extremely invasive.

Less invasive techniques for restricting absorption have been suggested. They include bariatric sleeve devices such as those disclosed in US Patent Application Publication Nos. 2004/0092892 and 2004/0107004. In these techniques, sleeves are passed through the duodenum so that chyme (the contents of the intestines) are passed through the sleeve and do not interact with the absorptive walls of the intestine. The sleeves may be perforated to permit some of the chyme material to pass through the walls of the small intestine and be absorbed as nutrients.

The bypass of the duodenum results in reduced absorption of desired nutrients (e.g., calcium) as well as undesirable nutrients (such as fat). Particularly, the loss of calcium absorption is significant since such loss can lead to osteoporosis.

Novel treatments include vagal modulation to block neural impulses on the vagus nerve to down-regulate pancreatic exocrine secretion production as well as alter gastric accommodation. Such treatments are shown in U.S. Patent Application Publication No. 2004/0172086 A1.

A suggestion has been made to divert the digestive enzymes from the pancreas past the duodenum. Such a suggestion is shown in US Patent Application Publication No. 2004/0092892 in which a tube is placed through the papilla and into the ducts of the gall bladder and the pancreas. A distal end of the tube is positioned significantly distal to the papilla such that pancreatic exocrine secretion and bile are diverted significantly distally to the papilla resulting in a reduction of absorption.

While pancreatic diversion is clinically interesting, cannulation of the pancreatic duct carries significant risks. Such cannulation of the pancreatic duct has been performed in endoscopic retrograde cholangiopancreatography (ERCP). Patients under-going ERCP and/or related procedures are known to having a higher likelihood of developing pancreatitis. It has been reported that the incidence of post-ERCP pancreatitis can be as high as 28%. Fazel et al., "Prophylactic Pancreatic Duct Stenting: A Panacea", *Gastroenterology*, Vol. 124, No. 4, pp. 1274-1275 (2003).

Pancreatitis is a serious disease with no effective treatment. While most patients suffering from acute pancreatitis or ERCP-induced pancreatitis recover after a short period of hospital stay with supportive care, a significant percent proceed to a severe stage of the disease in which necrosis of pancreatic tissue occurs. This extremely serious disease is characterized by an over-active pancreas which excretes digestive enzymes to such an extent that the pancreas itself is digested. The disease can be extremely painful. In many cases, the disease is fatal. The number of US patients who suffer an episode of acute pancreatitis is approximately 185,000 annually. Baron, et al., "Acute Necrotizing Pancreatitis", *New England J. of Medicine*, Vol. 340, No. 18, pp. 1412-1417 (1999). No definitive therapy is currently available to treat these patients except supportive care. Furthermore, the overall mortality rate for severe pancreatitis is about 20 to 30%. Id.

In addition to the serious health consequences, pancreatitis is costly. A recent study reported that the average total hospital cost to obtain a survivor of severe, acute pancreatitis is nearly $130,000 with an average length of hospital stay of 40 days. Soran, et al., "Outcome and quality of life of patients with acute pancreatitis requiring intensive care", *J. Surg. Res.*, 91(1), pp. 89-94 (2000). Further complicating the management of these patients is the uncertainty surrounding the prognosis because the course of the disease is unpredictable at initial presentation. Chatzicostas, et al., "Balthazar computed tomography severity index is superior to Ranson criteria and APACHE II and II scoring systems in predicting acute pancreatitis outcome", *J. Clinical Gastroenterology*, 36(3), pp. 253-260 (2003). Pancreatitis may be associated with a number of etiologies including chronic alcoholism or gallstones (e.g., gallstones lodged in the pancreatic or common duct). When acute pancreatitis becomes severe, treatment options are severely limited. Morbidity and mortality rates for pancreatitis are sobering. Baron, et al., "Acute Necrotizing Pancreatitis", *New England J. of Medicine*, Vol. 340, No. 18, pp. 1412-1417 (1999) and Steer et al., "Chronic Pancreatitis", *New England J. of Medicine*, pp. 1482-1490 (1995).

Accordingly, malabsorption bariatric treatments which contemplate cannulation of the pancreatic duct present unacceptable risks to patients and unacceptable societal costs.

It is an object of the present invention to provide a technique for pancreatic diversion in a manner, which minimizes risks of pancreatic duct obstruction and other associated morbidity.

SUMMARY OF THE INVENTION

According to a preferred embodiment of the present invention, a method and apparatus are disclosed for treating a patient's health condition by diverting pancreatic exocrine secretions. The apparatus includes a flow diverter of material compatible with chronic residence within a small intestine of the patient. The flow diverter has a cover end and a discharge end. The flow diverter is sized to be placed within the small intestine with the discharge end placed distally from said cover end and with said flow diverter further sized so permit passage of chyme through the small intestine and past the flow diverter. The cover end is sized to cover a discharge papilla of the pancreatic duct. The diverter is adapted to divert at least a portion of pancreatic exocrine secretion from the papilla to the distal discharge end.

BRIEF DESCRIPTION OF THE DRAWINGS

FIG. 3 is a side-sectional view of a wall of the small intestine at a duct papilla and showing the present invention as a flow diverter with a cover end covering the papilla;

FIG. 4 is the view of FIG. 3 showing an alternative embodiment for securing the cover end of the flow diverter over the papilla;

FIG. 5 is the view of FIG. 3 showing a still further alternative embodiment for securing the cover end of the flow diverter over the papilla;

FIG. 6 is an elevation view of the apparatus of FIG. 5 secured to an intestinal wall;

FIG. 7 is a view similar to FIG. 3 showing an alternative embodiment of a flow diverter;

FIG. 8 is an elevation view of the apparatus of FIG. 7 secured to an intestinal wall;

FIG. 9 is a view similar to FIG. 3 showing a still further alternative embodiment of a flow diverter with an attachment ring;

FIG. 10 is an elevation view of the apparatus of FIG. 9 secured to an intestinal wall not showing the diverter in place and showing an attachment ring in place;

FIG. 11 is a view similar to FIG. 3 showing a yet further alternative embodiment of a flow diverter; and FIG. 12 is an elevation view of the apparatus of FIG. 11 secured to an intestinal wall.

DETAILED DESCRIPTION OF THE PREFERRED EMBODIMENT

Referring now to the several drawing figures in which identical elements are numbered identically throughout, a description of the preferred embodiment of the present invention will now be provided. The disclosures of the following United States patent applications are incorporated herein by reference: U.S. Patent Application Publication No. 2004/0092892, U.S. Patent Application Publication No. 2004/0107004, and U.S. Patent Application Publication No. 2004/0172086.

Figure 1:
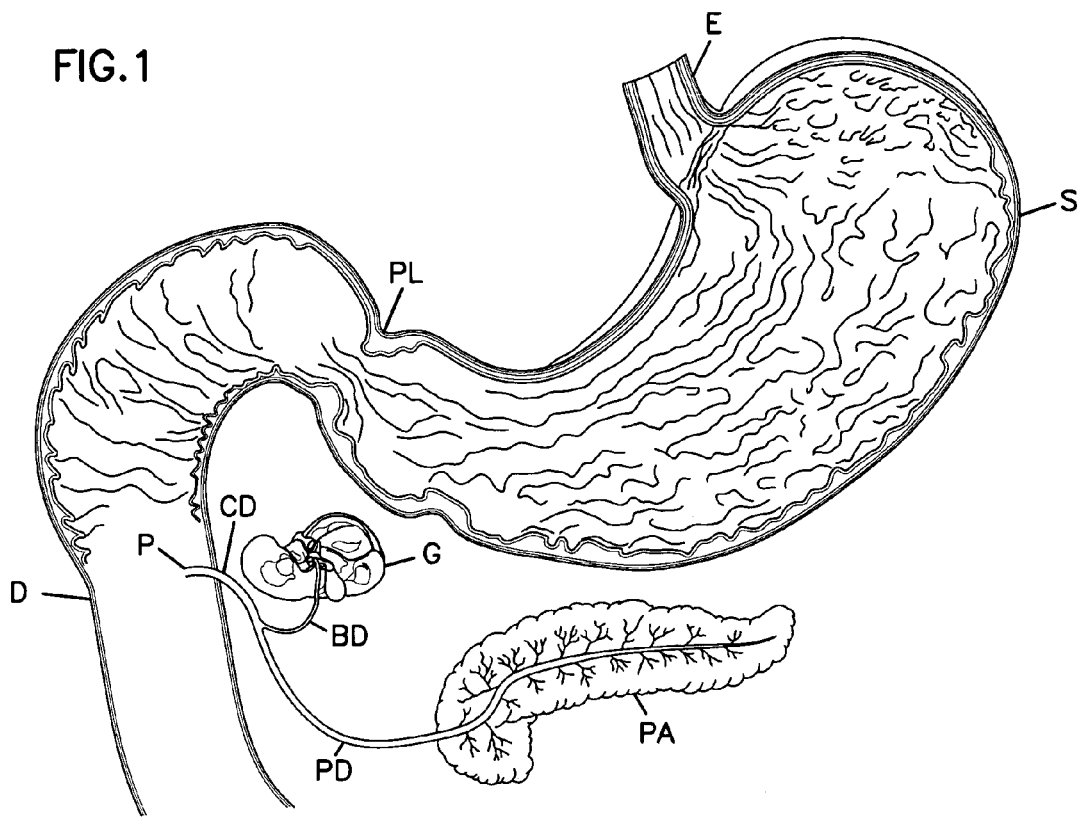
FIG. 1 is a schematic, side-sectional view of a portion of the gastro-intestinal system including stomach, upper small intestine, pancreas, gall bladder and associated ducts.

To facilitate an understanding of the use of the present invention, FIG. 1 provides a schematic illustration of relevant aspects of a patient's gastro-intestinal anatomy. As shown in FIG. 1, food passes through the esophagus E into the stomach S. The contents of the stomach S pass through the pylorus PL into the small intestine. The region of the small intestine directly distal to the pylorus PL is the duodenum D.

The lining of the duodenum D includes a mucosal layer adapted to absorb nutrients from the contents (referred to "chyme") of the intestine. The pancreas PA produces exocrine secretions (PES). The include lipase for breaking down fats and tripsin for breaking down proteins. The contents of the duodenum D flow through the remainder of the small intestine including the jejunal region for further nutrient absorption.

The pancreatic exocrine secretions pass through a pancreatic duct PD, which merges into the common duct CD for discharge into the duodenum. The common duct CD enters the duodenum D at a protrusion referred to as the papilla P. In the drawing figures, the length and diameter of the papilla P are exaggerated for ease of illustration.

The gall bladder G produces bile, which passes through the bile duct BD into the common duct CD. In some patients, the bile duct BD passes into the duodenum directly through a papilla, which is close approximation to the papilla P of the pancreatic duct PD. It will be appreciated that the present invention is applicable to such patients as well as the patient illustrated in FIG. 1.

Figure 2:
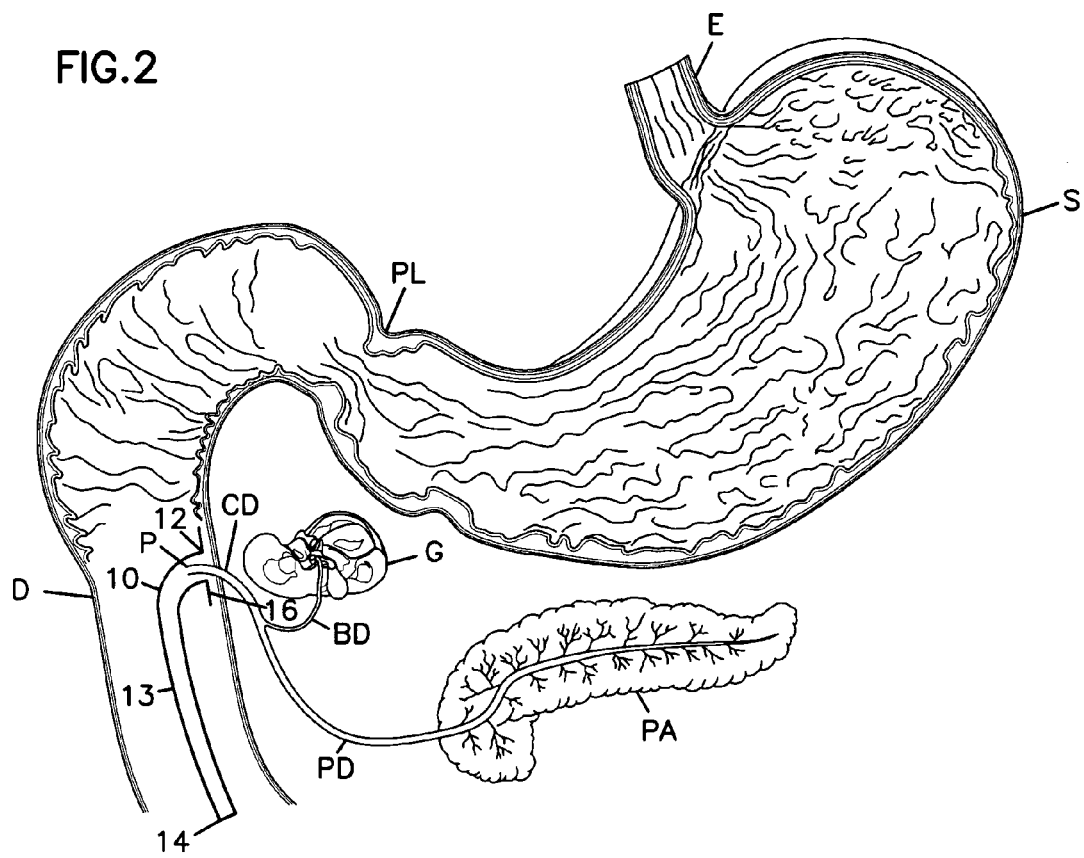
FIG. 2 is the view of FIG. 1 with a pancreatic flow diverter according to the present invention placed with the small intestine.

FIG. 2 schematically illustrates a pancreatic exocrine secretion (PES) diverter 10 positioned in the duodenum D. In the schematically illustrated embodiment of FIG. 2, the diverter 10 has a cover end 12 and a discharge end 14. The body 13 of the diverter between the cover end 12 and the discharge end 14 is a flexible tube which is sized to be received within the duodenum D. The tubular body 13 defines a conduit for directing flow of PES from the cover end 12 to the discharge end 14. The discharge end 14 is open to permit the PES to be discharged into the duodenum D. The diverter 10 is sized to fit within the duodenum but not to block the cross-section of the duodenum D such that chyme may continue to flow distally past the diverter.

The diverter 10 is sized to be placed within the small intestine with the cover end 12 covering and surrounding the discharge location of the PES fluid from the common duct CD at the papilla P. An annular flange 16 surrounds the cover end 12 and opposes the mucosal wall of the duodenum D surrounding the papilla P.

The diverter 10 may have a length such that the discharge end 14 terminates in the duodenum or in the jejunum. Further, in use, the length of the diverter 10 can be modified post-procedure to permit endoscopic access to the discharge end 14 and to trim off lengths of the diverter 10 as may be desired to increase nutrient absorption in a treated patient.

It will be noted that with the present invention, no portion of the diverter 10 protrudes into the common duct CD or the pancreatic duct PD. Accordingly, the design of diverter 10 reduces risks of developing post-procedure pancreatitis.

With the diverter 10 positioned as illustrated in FIG. 2, pancreatic exocrine secretion are diverted distally in the duodenum D (or jejunum) thereby reducing the length of the duodenum D in which pancreatic exocrine secretions are breaking down fats and proteins. This reduces the amount of absorption of such nutrients and their caloric effect.

The length of the diverter 10 can be selected such that the discharge end 14 extends into the jejunum to further reduce the amount of nutrient absorption. Since chyme continues to flow within the duodenum, nutrients (such as calcium) not requiring breakdown by bile or pancreatic secretions may continue to be absorbed to the duodenum and jejunum.

The interior wall of the duodenum is a mucosal surface M whose secretions can interfere with tissue in-growth to any implant such as the diverter 10. FIGS. 3-6 illustrate alternative techniques for securing the cover end 12 in place surrounding and covering the papilla P. As shown in FIG. 3, the flange 14 abuts the wall of the duodenum D and can be secured thereto by a plurality of sutures 18. Preferably, any suitable bio-adhesive can also be placed at the interface of the flange 16 and mucosal surface M to further adhere and seal the flange 16 against the mucosal surface M.

In FIG. 4, a stent 20 is placed within the papilla P and is expanded to an expanded state. It will be appreciated that expandable stents form no part of this invention per se and such stents are widely known in the medical device art. In the embodiment of FIG. 4, the diverter 10' has a cover end 12' which is sized to be received over and abutting the exterior surface of the papilla P. A crimp 22 surrounds the cover end 12' overlying the papilla P. The crimp 22 may be crimped through any suitable means to crimp the cover end 12' against the papilla P. The stent 20 acts as a mandrel to support the crimping and to prevent collapse of the papilla P.

FIG. 5 illustrates a further embodiment where the flange 16 is crimped in an annular crimp ring 40 surrounding the papilla P. It will be appreciated that crimping the tissue of gastro-intestinal organs is well known. Examples of such are commercially available products such as the Bard EndoCinch® tissue cinching tool and the Wilson-Cook Sewright®. These products crimp tissue in the esophagus and in the stomach for the treatment of gastro-esophageal reflux disease or for gastric partitioning.

The crimping action results in the exterior surface (the serosal tissue ST) of the duodenum D abutting in the region of the crimp 40. A suture 18 may be passed through the crimped flange 16 and duodenal tissue as illustrated in FIG. 5. Alternatively, a clip 24 may be placed over the crimped flange 16 and duodenal tissue to hold the crimp 40 in place. Over time, the opposing serosal tissue ST can adhere to further maintain the crimp 40.

With any of the forgoing, the cover end 12, 12' is secured to the duodenum D with the cover 12, 12' surrounding the papilla P such that pancreatic exocrine secretions from the papilla P discharge into the diverter 10 and are diverted down the length of the duodenum D any desired length or into the jejunum for discharge at the discharge end 14 of the diverter 10.

The diverter 10 may be at least partially permeable to the secretions to permit a portion of the secretions to pass through the wall of the diverter 10. In the figures, the partial permeability is illustrated by holes 26 formed through the wall of the diverter 10. Alternatively, the partial permeability can be provided through material selection of the diverter 10.

Post-operatively, the length of the diverter 10 can be trimmed as previously described or the entire length of the diverter 10 can be removed at the papilla P to expose the papilla P directly into the duodenum D to reverse the procedure. The papilla P and pancreatic duct PD are not invaded by the present invention thereby reducing risk of post-operative pancreatitis.

In all the previous embodiments, the diverter 10, 10' has been shown and described as a tubular member, which defines the fluid flow conduit for pancreatic exocrine secretions from the papilla P. FIGS. 7 and 8 illustrate an alternative embodiment.

In FIGS. 7 and 8, the diverter 10" includes a sheet material 13" having a closed cover end 12" and a flange 16" which surrounds the longitudinal side edges of the diverter 10" as well as the upper edge of the cover end 12". The flange 16" is secured to the wall of the duodenum D through any suitable means such as those previously described. The discharge end 14 is not secured to the duodenal wall D. As a result, the opposing surfaces of the duodenum D and the wall 13" of the diverter 10" act as the flow conduit for diverting PES flow from the papilla P distally to the discharge end 14. As in the previous embodiment, the diverter 10" may be semi-permeable as illustrated by holes 26".

FIGS. 9 and 10 illustrate an alternative embodiment of a diverter 10'''. An attachment ring 16''' is provided secured to the intestinal wall D surrounding the papilla P. The ring 16''' can be attached through any suitable means such as adhesive or sutures. FIG. 10 illustrates the ring 16''' attached to the wall D by clips 24''' crimped over material of the wall D at the crimp location similar to the crimping described with reference to FIG. 5. In FIG. 10, the portion of the ring 16''' not crimped with tissue and held by clips 24''' is exposed. The cover end 12''' of the diverter 10''' is attached to the ring 16''' (e.g., by sutures not shown).

With this embodiment, the procedure is easily reversed by detaching the diverter 10''' from the ring 16''' (e.g., by severing sutures) leaving only the ring 16''' in place and fully exposing the papilla P. Such reversal makes the present invention particularly suitable for morbidly obese patients who are not candidates for other bariatric surgeries due to surgical risks. The present invention may be a temporary bridge to such surgeries by inducing a weight loss in such patients to the extent they can more safely tolerate more invasive surgical bariatric procedures. While this removable procedure is shown in the use of a tubular diverter 10''', it can be used with any of the embodiments.

FIGS. 11 and 12 illustrate an alternative to the embodiment of FIGS. 7 and 8. These figures also illustrate the use of tissue crimping with clips 24'' '' to hold the cover end 12''' over the papilla. Unlike FIGS. 7 and 8, the side walls 10a'''' of the diverter 10'''' are not attached to the intestine D. Instead, the diverter 10'''' is a flap covering the papilla P and extending distally in the intestine. If desired, the side edges 10a'''' can be tacked to the wall D at spaced locations by sutures, adhesives, clips or the like to prevent proximal migration or twisting of the flap diverter 10''''.

The present invention many be endoscopically delivered and provide the benefits of a malabsorption procedure without the extreme invasiveness of traditional gastric bypass procedures and without the significant risk of pancreatitis and other maladies associated with cannulation of the pancreatic duct. Further, the present invention may be utilized in conjunction with other procedures such as surgical or minimally invasive procedures for reducing gastric volume.

U.S. patent application Publication No. 2004/0092892 describes permeability of materials for a tube for directing PES. As in that disclosure, the diverter 10, 10', 10'' may be semi-permeable, allowing certain materials from the intestine to pass into the tube, such as acids. Alternatively, the portion of the device in the intestine may only allow certain materials from inside the device to permeate out, such as bases to neutralize stomach acids.

The lumen of the diverter 10, 10', 10'' is preferably of a diameter to allow flow of bile and pancreatic secretions. Optionally, the diverter tube may be constructed with flexible walls to allow peristaltic motions of the intestinal wall to effect movement of bile and pancreatic juices through the diverter tube.

The interior and/or exterior of the diverter tube can optionally be formed from a relatively inert material such as a polyolefin (e.g. polyethelene) or a fluoropolymer (e.g. FEP or PFA) or coated with a low friction material (e.g. a hydrogel) to reduce friction of bile and pancreatic juices (interior) and reduce native luminal irritation (exterior). The interior of the diverter tube can optionally include a coating to resist crystallizing and/or deposition of bile and pancreatic secretions which could obstruct flow through the tube. The wall of the diverter tube may be reinforced with rings or a spiral made of wire and/or plastic. Optionally the diverter tube can include means for stabilization at the distal end such as a brush, weight, or inflatable balloon.

Typically, the device will be 50-510 cm in length and have an inner diameter of 1.0-7.5 mm. The device 10, 10', 10'' could be made from a silicone, polyurethane, polyethylene or a fluoropolymer such as PFA. Device coatings could include hydrogels such as PVP (polyvinylpyrolidone or other coating such as parylene as described herein. Preferably, the diverter tube is constructed with radiopaque and/or sonoreflective materials and/or includes one or more radiopaque and/or sonoreflective markers for enhanced imaging by X-ray, fluoroscopy and/or ultrasonic imaging so that the position and functional state of the implanted intestinal sleeve can be verified non-invasively.

It has been shown how the objects of the invention have been attained in a preferred manner. Modifications and equivalents of the disclosed concepts are intended to be included within the scope of the appended claims.

We claim:

1. An apparatus for treating a health condition susceptible to treatment by reduction of nutrient absorption, said apparatus comprising:

a flow diverter of material compatible with chronic residence within a small intestine of a patient, said flow diverter having a cover end and a discharge end, said flow diverter comprising a flap of material having a front and a back surface separated by left and right side edges;

said flow diverter sized to be placed within said small intestine with said discharge end placed distally from said cover end and with said flow diverter further sized to permit passage of chyme through said small intestine and past said flow diverter;

said cover end sized to cover a discharge location of pancreatic exocrine secretions into a small intestine of said patient and adapted to be attached to an attachment ring located in the small intestine at said discharge location, wherein said front surface of said flap of material opposes said discharge location of said small intestine;

said diverter adapted to divert at least a portion of pancreatic exocrine secretion from said discharge location to said distal discharge end with said front surface of said flap of material opposing said discharge location of said small intestine and defining there between a flow path in fluid flow communication with said discharge location with said flow path in surface contact with a length of said small intestine between said discharge location and said discharge end.

2. An apparatus according to claim 1 wherein said material of said diverter is at least partially permeable to said pancreatic exocrine secretion to permit a portion of the secretions to pass through the material of the flow diverter.

3. An apparatus according to claim 2 wherein said diverter includes a plurality of holes through a wall of said diverter along a length of said diverter.

4. An apparatus according to claim 1, wherein said diverter is a flap of material sized to extend distally to said discharge location papilla, and with side edges unattached to said wall of said small intestine, with opposing surfaces of said diverter and said wall of said small intestine between said sides defining a flow conduit.

5. A method for treating a health condition susceptible to treatment by reduction of nutrient absorption, said method comprising:

selecting a patient for treatment;

accessing a discharge location of pancreatic exocrine secretions into a small intestine of the patient;

placing an apparatus of claim 1 into said small intestine by a) covering said discharge location with the cover end of a flow diverter, wherein the flow diverter comprises a flap of material having a front and a back surface separated by left and right side edges;

b) positioning said flow diverter in said small intestine with the cover end positioned over said discharge location and a discharge end positioned distally to said discharge location, wherein said front surface of said flap of material opposes said discharge location of said small intestine and defines there between a flow path in fluid flow communication with said discharge location, with said flow path in surface contact with a length of said small intestine between said discharge location and said discharge end; and c) securing said cover end to an attachment ring located in said small intestine at said discharge location.

6. A method according to claim 5 wherein said flow diverter is selected to have a size to be placed chronically within said small intestine without complete blockage of passage of chyme through said small intestine.

7. A method according to claim 5 wherein said left and right side edges are adapted to be secured to a wall of said small intestine and said method including securing said side edges to said wall of said small intestine.

8. A method according to claim 7 wherein said side edges are secured to said wall of said small intestine at intervals with detached lengths of said side edges between said intervals.

9. A method according to claim 7 wherein said side edges are secured to said wall of said small intestine continuously along a length of said side edges.

10. A method for treating a health condition susceptible to treatment by reduction of nutrient absorption, comprising:

selecting a patient for treatment;

positioning an apparatus of claim 1 in a small intestine of the patient with a cover end positioned over a discharge location of pancreatic exocrine secretion into said small intestine, and a discharge end positioned distally to said discharge location, wherein said front surface of said flap of material opposes said discharge location of said small intestine and defines there between a flow path in fluid flow communication with said discharge location with said flow path in surface contact with a length of said small intestine between said discharge location and said discharge end, and securing said cover end to an attachment ring located in said small intestine at said discharge location.

11. The method according to claim 10, wherein said flow diverter is selected to have a size to be placed chronically within said small intestine without complete blockage of passage of chyme through said small intestine.

12. The method according to claim 10, wherein said flow diverter comprises a flap of material having a front and a back surface separated by left and right side edges, and wherein said left and right side edges are adapted to be secured to a wall of said small intestine and said method including securing said side edges to said wall of said small intestine.

13. The method according to claim 12, wherein said side edges are secured to said wall of said small intestine continuously along a length of said side edges.

* * * * *